(12) United States Patent
Tamaki et al.

(10) Patent No.: US 7,312,189 B2
(45) Date of Patent: Dec. 25, 2007

(54) AGENT FOR TREATMENT OF INFLAMMATORY BOWEL DISEASE

(75) Inventors: Hiroyuki Tamaki, Kyoto (JP); Hajime Nakamura, Hirakata (JP); Junji Yodoi, Kyoto (JP); Kazuichi Okazaki, Kyoto (JP); Akiyoshi Nishio, Tenri (JP); Tsutomu Chiba, Kyoto (JP)

(73) Assignee: Redox Bioscience Inc., Kyoto-Fu (JP)

( * ) Notice: Subject to any disclaimer, the term of this patent is extended or adjusted under 35 U.S.C. 154(b) by 0 days.

(21) Appl. No.: 10/748,490

(22) Filed: Dec. 30, 2003

(65) Prior Publication Data

US 2006/0110378 A1    May 25, 2006

(51) Int. Cl.
*A61K 38/16* (2006.01)
*A61K 38/17* (2006.01)

(52) U.S. Cl. .......................................... 514/2; 514/885

(58) Field of Classification Search ...................... None
See application file for complete search history.

(56) References Cited

OTHER PUBLICATIONS

Sido et al (2005), European Journal of Immunology, pp. 408-417.*
Claudio Fiocchi, "Inflammatory Bowel Disease: Etiology and Pathogenesis," Gastroenterology: 115, pp. 182-205 published in 1998.
Tagaya, et al., "ATL-derived factor (ADF), an IL-2 receptor/Tac inducer homologous to thioredoxin; possible involvement of dithiol-reduction in the IL-2 receptor induction," The EMBO Journal vol. 8, No. 3, pp. 757-764 published in 1989.
Powis, et al., "Properties and Biological Activities of Thioredoxins," Annual Reviews in Biphysics and Biomolecular Structure: 30 pp. 421-455 published in 2001.
Lih-Brody, et al., "Increased Oxidative Stress and Decreased Antioxidant Defenses in Mucosa of Inflammatory Bowel Disease," Digestive Diseases and Science, vol. 41, No. 10 pp. 2078-2086 published in 1996.
McKenzie, et al., "Evidence of Oxidant-induced Injury to Epithelial Cells during Inflammatory Bowel Disease," Journal Clinical Investigation vol. 98, pp. 136-141 published in 1996.
Korenaga, et al., "Impaired Antioxidant Defense System of Colonic Tissue and Cancer Development in Dextran Sulfate Sodium-Induced Colitis in Mice," Journal of Surgical Research 102, pp. 144-149 published in 2002.
Okayasu, et al., "A Novel Method in the Induction of Reliable Experimental Acute and Chronic Ulcerative Colitis in Mice," Gastroenterology; 98 pp. 694-702 published in 1990.
Ohkawara, et al., "Amelioration of Dextran Sulfate Sodium-Induced Colitis by Anti-macrophage Migration Inhibitory Factor Antibody in Mice," Gastroenterology; 123 pp. 256-270 published in 2002.
Jeffers, et al., "A Novel Human Fibroblast Growth Factor Treats Experimental Intestinal Inflammation," Gastroenterology; 123. pp. 1151-1162 published in 2002.
Williams, et al., "Enhanced Survival and Mucosal Repair After Dextran Sodium Sulfate-Induced Colitis in Transgenic Mice That Overexpress Growth Hormone," Gastroenterology; 120 pp. 925-937 published in 2001.
Kruidenier, et al., "Review article: oxidative stress as a pathogenic factor in inflammatory bowel disease—radicals or riduculous?" Alimentart Pharmacology & Therpeutics; 16 pp. 1997-2015 published in 2002.
Nakamura, et al., "Circulating thioredoxin suppresses lipopolysaccharide-induced neutrophil chemotaxis," Proceedings of the National Academy of Science of the United States of America vol. 98, No. 26 pp. 15143-15148 published in Dec. 18, 2001.
Nakamura, et al., "Chronic elevation of plasma thioredoxin: Inhibition of chemotaxis and curtailment of life expectancy in AIDS," Proceedings of the National Academy of Science of the United States of America vol. 98, No. 5 pp. 2688-2693 published in Feb. 27, 2001.
Powis, et al., "Properties and Biological Activities of Thioredoxins," Annual Reviews of Pharmacology and Toxicology 41 pp. 216-295 published in 2001.

* cited by examiner

*Primary Examiner*—Prema Mertz
(74) *Attorney, Agent, or Firm*—Knobbe, Martens, Olson & Bear, LLP (57) ABSTRACT

The present invention provides a therapeutic agent for treating inflammatory bowel diseases comprising as an active ingredient at least one member selected from polypeptides belonging a family exhibiting thioredoxin activity.

6 Claims, 10 Drawing Sheets

Fig. 1. Serial change of percentage body weight of the DSS model in TRX-Tg mice

Fig. 2. Colon length and bloody stool score of the DSS model in TRX-Tg mice

Fig. 3. Photomicrographs of H&E-stained sections of distal colon of the DSS model in TRX-Tg mice

Fig. 4-A. Histological score of the DSS model in TRX-Tg mice

*Inflammation extent*

*Inflammation severity*

Fig. 4-B. Histological score of the DSS model in TRX-Tg mice

*Crypt damage*

*Total colitis*

Fig. 5. Serial change of percentage body weight of treatment protocol with human TRX (5mg/kg i.p.)

Fig. 6. Colon length of treatment protocol with human TRX (5mg/kg i.p.)

Fig. 7. Photomicrographs of H&E-stained sections of distal colon of treatment protocol with human TRX (5mg/kg i.p.)

Fig. 8-A. Histological score of treatment protocol with human TRX (5mg/kg i.p.)

Fig. 8-B. Histological score of treatment protocol with human TRX (5mg/kg i.p.)

US 7,312,189 B2

AGENT FOR TREATMENT OF INFLAMMATORY BOWEL DISEASE

TECHNICAL FIELD

The present invention relates to a prophylactic and therapeutic agent for treating an inflammatory bowel disease, and a therapeutic method using such an agent.

BACKGROUND ART

Inflammatory bowel diseases (IBD), such as Crohn's disease and ulcerative colitis, are intractable diseases repeating the regression and exacerbation of their pathological states. The cause of these diseases has not yet become clear although autoimmune disorders, *enterobacilli*, etc., are presumed to be involved (Fiocchi C. Inflammatory bowel disease: etiology and pathogenesis. Gastroenterology 1998; 115: 182-205). Currently, various medications are given to treat IBD; however, some patients cannot continue therapy because conventional treatments fail to regress their pathological conditions or because of the side effects of the medications. For those cases in which medications cannot rectify pathological conditions, surgery to remove the gastrointestinal tract is unavoidable. Therefore, in view of QOL (Quality of Life), the development of medications that are effective and pose little side effects is in demand.

It is known that oxidative stress caused by reactive oxygen species is involved in various inflammatory reactions including colitis. Redox regulation, a series of mechanisms regulating intracellular signaling, produces or eliminates reactive oxygen species to control intracellular signaling. Thioredoxin (TRX) is one of the principal factors responsible for this redox regulation. TRX is a multifunctional molecule that has been cloned as an adult T cell leukemia-derived factor and has the ability to control redox reactions by the thiol-disulfide reaction of the Cys-Gly-Pro-Cys sequence (SEQ ID NO:1) (Tagaya Y, Maeda Y, Mitsui A, Kondo N, Matsui H, Hamuro J, Brown N, Arai K, Yokota T, Wakasugi H, ATL-derived factor (ADF), an IL-2 receptor/Tac inducer homologous to thioredoxin; possible involvement of dithiol-reduction in the IL-2 receptor induction. Embo J 1989; 8: 757-64). Various reports disclose functions of TRX, such as the inhibition of apoptosis and enhancement of cytophylaxis reaction by diminishing the reduction or production of reactive oxygen species (ROS), activating transcription factors such as NF-kB, Refi, etc., inhibiting signal transduction to MAPK by ASK-1 inactivation (Powis G, Montfort WR. Properties and biological activities of thioredoxins. Annu Rev Biophys Biomol Struct 2001; 30: 421-55). Accordingly, TRX is known to be involved in enhancing biophylaxis.

In IBD-affected mucosal tissues, although the production of ROS is increased, the production of antioxidative molecules, such as Cu/Zn-SOD, reduced thiols, and the like, is decreased (Lih-Brody L, Powell S R, Collier K P, Reddy G M, Cerchia R, Kahn E, Weissman G S, Katz S, Floyd R A, McKinley MJ, Fisher S E, Mullin G E. Increased oxidative stress and decreased antioxidant defenses in mucosa of inflammatory bowel disease. Dig Dis Sci 1996; 41: 2078-86; McKenzie S J, Baker M S, Buffinton G D, Doe W F. Evidence of oxidant-induced injury to epithelial cells during inflammatory bowel disease. J Clin Invest 1996; 98: 136-41). Therefore, it is said that IBD-affected lesions face an imbalance in the production of ROS and antioxidative molecules.

Likewise, in the lesions of dextran sulfate sodium (DSS)-induced inflammatory bowel diseases, which are IBD models, a decrease in the production of antioxidative molecules is reported (Korenaga D, Takesue F, Kido K, Yasuda M, Inutsuka S, Honda M, Nagahama S. Impaired antioxidant defense system of colonic tissue and cancer development in dextran sulfate sodium-induced colitis in mice. J Surg Res 2002; 102: 144-9). These DSS-induced colitis model are likely to exhibit the pathological conditions of relatively reproducible colitis (Okayasu I, Hatakeyama S, Yamada M, Ohkusa T, Inagaki Y, Nakaya R. A novel method in the induction of reliable experimental acute and chronic ulcerative colitis in mice. Gastroenterology 1990; 98: 694-702), and are widely used in evaluating therapeutic effects of medical agents.

The inventors found that thioredoxin produces colitis-inhibiting effects using DSS-induced colitis model mice, and have accomplished the present invention based on this finding.

An object of the invention is to provide a prophylactic and therapeutic agent for an inflammatory bowel disease comprising thioredoxin as an active ingredient, and a method for treating an inflammatory bowel disease using such an agent.

SUMMARY OF THE INVENTION

The present invention relates to a prophylactic and therapeutic agent for treating an inflammatory bowel disease comprising as an active ingredient at least one polypeptide belonging to a family having thioredoxin activity, and a method for treating an inflammatory bowel disease using such an agent.

BRIEF DESCRIPTION OF THE DRAWINGS

FIG. 2-A shows the colon lengths of TRX-Tg DSS colitis model mice (Tg-DSS), wild-type DSS colitis model mice (Wt-DSS), and the control mice (wild type: Wt).

FIG. 2-B shows the Bloody stool scores of TRX-Tg DSS colitis model mice (Tg-DSS) and wild-type DSS colitis model mice (Wt-DSS).

FIG. 4-A shows the Histological scores (inflammation severity and inflammation extent) of TRX-Tg DSS colitis model mice (Tg-DSS), wild-type DSS colitis model mice (Wt-DSS), and the control mice (C57BL/6).

FIG. 4-B shows the Histological scores (crypt damage and total colitis) of TRX-Tg DSS colitis model mice (Tg-DSS), wild type DSS colitis model mice (Wt-DSS), and the control mice (C57BL/6).

FIG. 8-A shows the Histological scores (inflammation severity and inflammation extent) of DSS colitis model mice (TRX 5 mg/kg-ip), wild-type DSS colitis model mice (Wt-DSS), and the control mice (Wt).

FIG. 8-B shows the Histological scores (crypt damage and total colitis) of DSS colitis model mice administered with rhTRX (TRX 5 mg/kg-ip), wild-type DSS colitis model mice (Wt-DSS), and the control mice (Wt).

DISCLOSURE OF THE INVENTION

Polypeptides belonging to the family having thioredoxin activity herein include a wide variety of peptides, for example, oligopeptides and polypeptides (proteins), insofar as they have thioredoxin activity.

The present invention provides the following therapeutic agents for treating an inflammatory bowel disease and methods for treating the same.

Item 1. A therapeutic agent for treating an inflammatory bowel disease comprising as an active ingredient at least one polypeptide belonging to a thioredoxin superfamily.

Item 2. The therapeutic agent according to Item 1 for treating an inflammatory bowel disease, the inflammatory bowel disease being ulcerative colitis or Crohn's disease.

Item 3. The therapeutic agent according to Item 1, wherein the at least one polypeptide belonging to the thioredoxin superfamily is human thioredoxin.

Item 4. A method for treating an inflammatory bowel disease, the inflammatory bowel disease being ulcerative colitis or Crohn's disease, the method comprising administering an effective amount of polypeptide belonging to a thioredoxin superfamily to a patient in need of the inflammatory bowel disease treatment.

Item 5. The method according to Item 5 comprising administering 1-100 mg of thioredoxin per kg body weight of an human adult.

The family exhibiting thioredoxin activity contains the sequence-Cys-X-Y-Cys-(SEQ ID NO:2) in the active site (wherein X and Y are the same or different amino acids selected from 20 kinds of natural amino acids and is called a thioredoxin superfamily (hereinafter sometimes referred to as the "TRX family").

Examples of polypeptides of the TRX family include those having the sequences: -Cys-Gly-Pro-Cys-(SEQ ID NO: 1), -Cys-Pro-Tyr-Cys-(SEQ ID NO:3), -Cys-Pro-His-Cys-(SEQ ID NO:4), or -Cys-Pro-Pro-Cys-(SEQ ID NO:5) in the active site. Among these, preferable are those having the sequence -Cys-Gly-Pro-Cys-(SEQ ID NO: 1) in the active site.

Specifically, examples of polypeptides belonging to the TRX family include thioredoxins derived from animals including humans (ADF derived from animals including humans), thioredoxins derived from bacteria such as *E. coli*, thioredoxins derived from yeasts, and other thioredoxins; polypeptides having human ADF activity (human ADFP); glutaredoxins derived from humans, *E. coli*, etc.; and the like.

Preferable polypeptides belonging to the TRX family are thioredoxins, and especially preferable are human and yeast thioredoxins. Yeast thioredoxins may be isolated from yeast or may be in the form of yeast containing significant amounts of thioredoxin.

Such polypeptides of the TRX family can be used alone or in combination in the therapeutic agent for treating an inflammatory bowel disease of the present invention.

Polypeptides belonging to the TRX family can be obtained from bacteria (e.g., *E. coli*), yeasts, plants, and animals, especially mammals (humans, cows, horses, dogs, cats, monkeys, guinea pigs, rats, mice, rabbits, etc.). Polypeptides belonging to the TRX family can be obtained according to methods for purifying natural products or according to genetic engineering using yeast, *E. coli*, etc. Polypeptides, insofar as exhibiting TRX activity, may be derivatives in which one or a plurality of, and preferably one or a few, amino acids are substituted, added, or deleted.

Polypeptides including thioredoxin can be either in the oxidized form or in the reduced form, but preferably in the reduced form.

Examples of intestinal diseases to be treated are inflammatory bowel diseases, for example, ulcerative colitis; Crohn's disease; infectious colitis caused by bacteria, parasites, viruses, fungi, etc.; drug-induced colitis caused by medicines, chemical compounds, etc.; irradiation colitis; ischemic colitis; obstructive colitis; solitary rectal ulcers; regional colitis; hemorrhagic colitis; etc.

Administrative routes for the therapeutic agent of the present invention for treating an inflammatory bowel disease can be either oral or parenteral, and suitably selected by clinicians. The active ingredient, thioredoxin, can be administered singly or in combination with conventional carriers.

When administered orally, the prophylactic and therapeutic agent of the invention may be in the form of tablets, coated tablets, powders, granules, capsules, pills, or like solid formulations; solutions, suspensions, emulsions, syrups, or like liquid formulations; aerosols, atomizers, nebulizers, or like inhalants; liposome-encapsulated formulations; etc.

When administered parenterally, the prophylactic and therapeutic agent of the invention may be in the injectable form (e.g., solutions, suspensions, etc.) intended for intravenous, subcutaneous, endodermic, intramuscular, intraperitoneal, and like injections; and may be in other forms such as solutions, suspensions, emulsions, drops, suppositories, ointments, etc.

When the prophylactic and therapeutic agent of the invention is in the form of a solution, it may be frozen and stored, or freeze-dried to remove its water content and stored. Freeze-dried formulations may be used by redissolving them in distilled water for injection or like liquid media.

Examples of pharmaceutically acceptable carriers for use in the prophylactic and therapeutic agent of the invention include diluents and excipients that are usually used according to the form of pharmaceutical preparation, such as binders, disintegrants, surfactants, absorption enhancers, humectants, adsorbents, lubricants, fillers, extenders, moisturizers, antiseptic agents, stabilizers, emulsifiers, solubilizers, salts for adjusting osmotic pressure, buffers, etc. These carriers are suitably selected according to the unit dosage form of the prophylactic and therapeutic agent.

Furthermore, colorants, preservatives, aroma chemicals, flavorings, sweeteners, and the like, as well as other pharmaceuticals may be used in the prophylactic and therapeutic agent of the invention if necessary.

The amount of polypeptide of the TRX family effective for treating an inflammatory bowel disease can be readily selected by a person skilled in the art in view of conventional techniques. For example, it is generally about 0.1 to about 100 mg, preferably about 0.1 to about 10 mg, and more preferably about 1 to about 10 mg, per kg body weight per day, which may be attained in 1-3 doses. It is preferable to select the amount according to the form of therapeutic agent, gender of the patient, age, degree of the disease, etc.

The prophylactic and therapeutic agent of the present invention can be used in steroid hormone therapy, which is currently the primary therapeutic method for inflammatory bowel diseases, thereby contributing to the reduction or withdrawal of the use of steroid hormones.

EXAMPLES

Examples are given below to illustrate the invention in more detail, but the scope of the invention is not limited to these examples.

Mice and Reagents

Female C57BL/6 mice (CLEA Japan, Shizuoka, Japan) aged of 9-11 weeks with a body weight of 20-22 g were used to produce control mice and dextran sulfate sodium (DSS)-induced colitis models. B6-derived thioredoxin transgenic (TRX-Tg) mice and recombinant human thioredoxin (rhTRX) were supplied by Ajinomoto Co., Inc.

It is known that inflammatory lesions such as mucosal tissue damage, inflammatory cell infiltration, submucosal edemas, ulceration, etc., are most notably observed in the distal colon of colitis model mice produced using high-molecular-weight DSS, thereby further influencing the dose dependency (Ohkawara T, Nishihira J, Takeda H, Hige S, Kato M, Sugiyama T, Iwanaga T, Nakamura H, Mizue Y, Asaka M. Amelioration of dextran sulfate sodium-induced colitis by anti-macrophage migration inhibitory factor antibody in mice. Gastroenterology 2002; 123: 256-70). Therefore, in the examples herein, the inventors examined the extent of tissue disorder in 1.5 cm of the colon situated next to the anus of colitis model mice produced using a solution of 3% DSS with a molecular weight of 36000-50000.

Comprehensive Evaluation of Colitis (a) Daily change of body weight (%) was calculated relative to the body weight at Day 0.

(b) The length of the colons removed was measured. Furthermore, the blood content in the feces of the TRX-Tg DSS-induced colitis model mice was evaluated according to the criteria of the Bloody stool score (Table 1; Jeffers M, McDonald W F, Chillakuru R A, Yang M, Nakase H, Deegler L L, Sylander E D, Rittman B, Bendele A, Sartor R B, Lichenstein H S. A novel human fibroblast growth factor treats experimental intestinal inflammation. Gastroenterology 2002; 123: 1151-62).

(c) 1.5 cm of the colon situated next to the anus was immobilized by 10% formalin solution. This specimen was further immobilized by paraffin, thinly sliced, and subjected to hematoxylin-eosin staining. This specimen was observed through an optical microscope.

(d) An histological evaluation was conducted on the specimen every 0.5 cm totaling 3 sites using the Histological scoring system shown in Table 2 (Williams K L, Fuller C R, Dieleman L A, DaCosta C M, Haldeman K M, Sartor R B, Lund P K. Enhanced survival and mucosal repair after dextran sodium sulfate-induced colitis in transgenic mice that overexpress growth hormone. Gastroenterology 2001; 120: 925-37). The scores of each site were averaged.

Statistical Analysis

The data were expressed as mean±standard error. The Histological scores were calculated by statistical software (Statview, Abacus Concepts, Berkeley, Calif.) and compared using the Student's t-Test. The results were deemed significantly different at $p<0.05$.

Example 1

Clinical and Histological Investigation of DSS-Induced Colitis in TRX-Tg Mice

C57BL/6 mice (Control Group, n=10) and TRX-Tg mice (Tg Group, n=10) were given 3% (w/v) DSS in their drinking water (MW: 36000-50000, ICN Pharmaceuticals Inc., Calif., USA) for 7 days. The body weight was measured daily from immediately before DSS administration (Day 0) till immediately before finishing DSS administration (Day 7). After finishing DSS administration, the mice were sacrificed by ether anesthesia, and the colons were removed to examine colitis.

Figure 1:
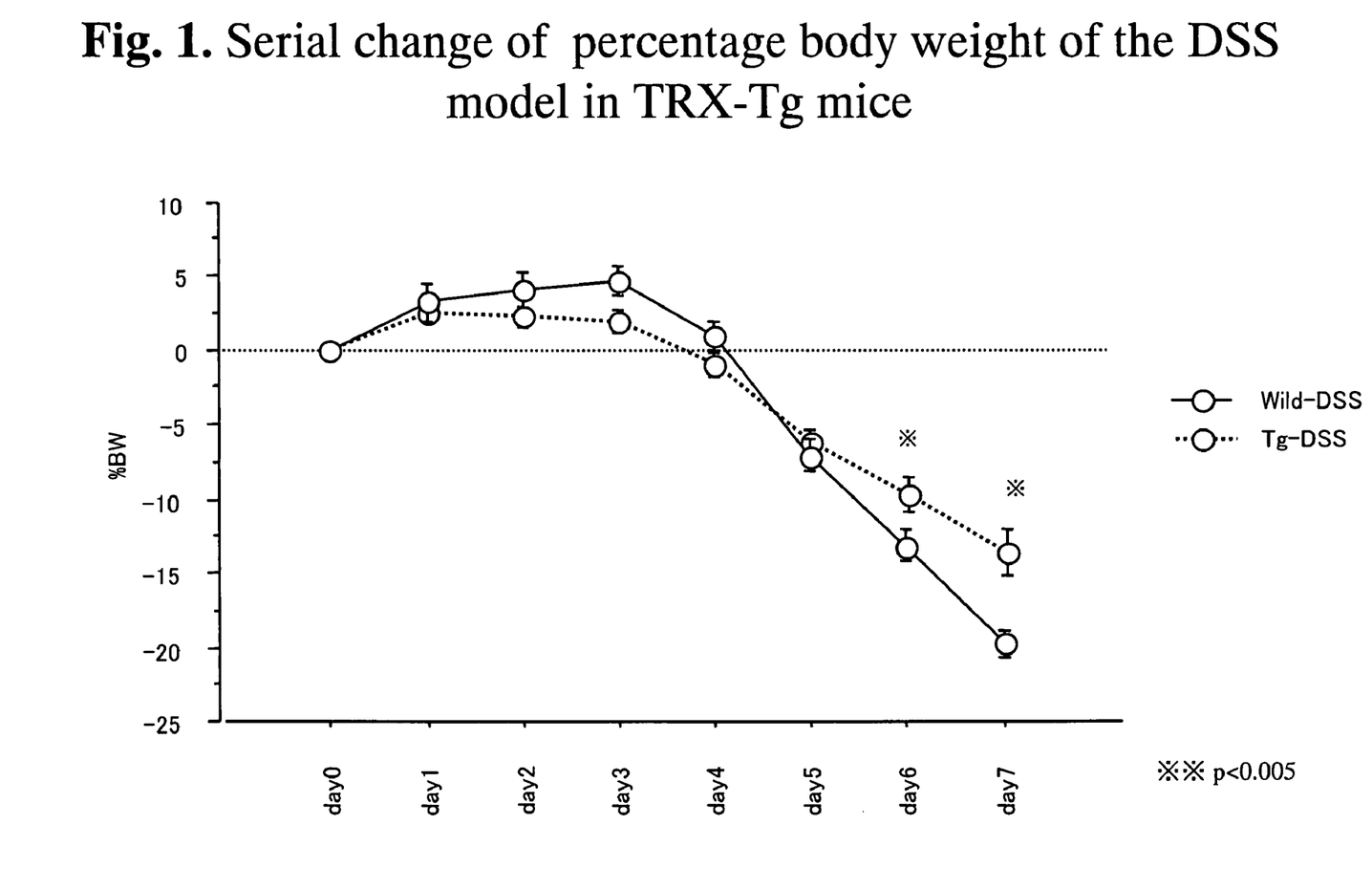
FIG. 1 shows the body weight changes, expressed in percentage, of thioredoxin-transgenic (TRX-Tg) DSS colitis model mice (Tg-DSS) and wild-type DSS colitis model mice (Wt-DSS) after DSS administration.
Figure 2:
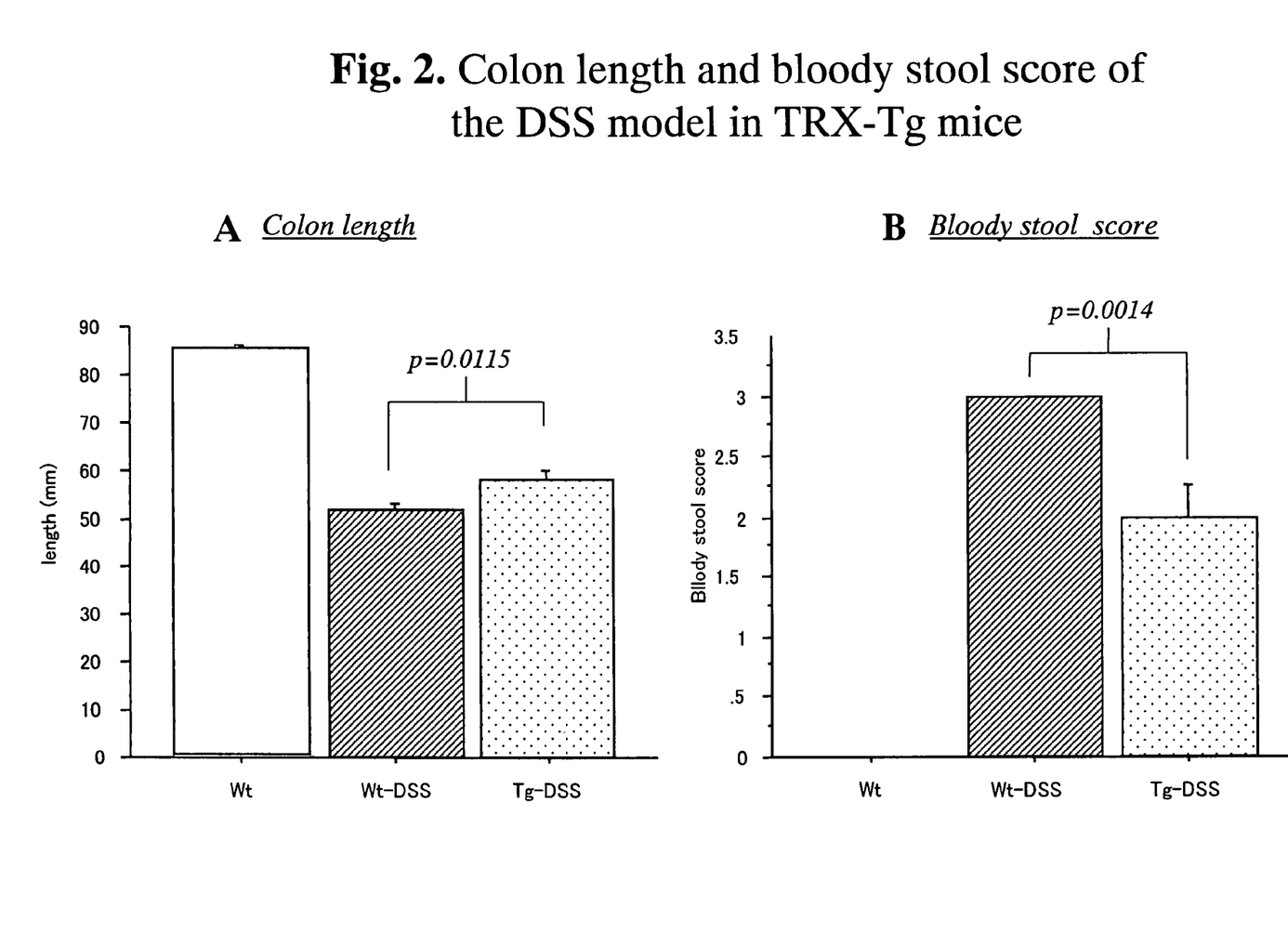

The body weight reduction was significantly smaller in the Tg Group than in the Control Group on Days 6 and 7 of the DSS administration (FIG. 1). When the length of the colons was measured, the average length of the colons of the Tg Group was significantly longer than that of the colons of the Control Group (FIG. 2-A). Likewise, with respect to the blood stool score, the Tg-DSS Group exhibited a significantly lower value than the Control Group (FIG. 2-B).

Figure 3:
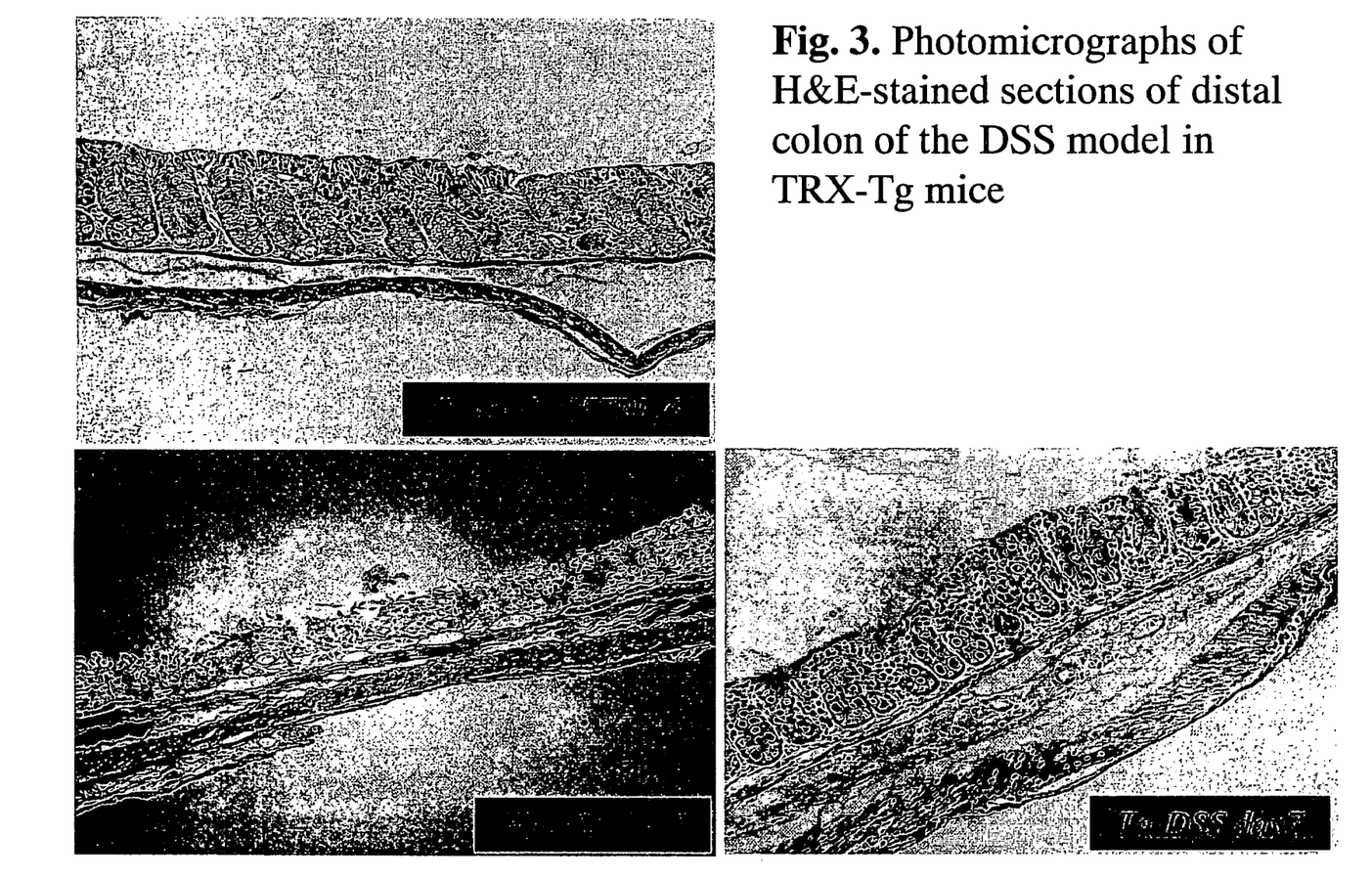
FIG. 3 shows HE (hematoxylin-eosin) staining of the distal colons of TRX-Tg DSS colitis model mice (Tg-DSS), wild-type DSS colitis model mice (Wt-DSS), and the control mice (C57BL/6).
Figure 4:
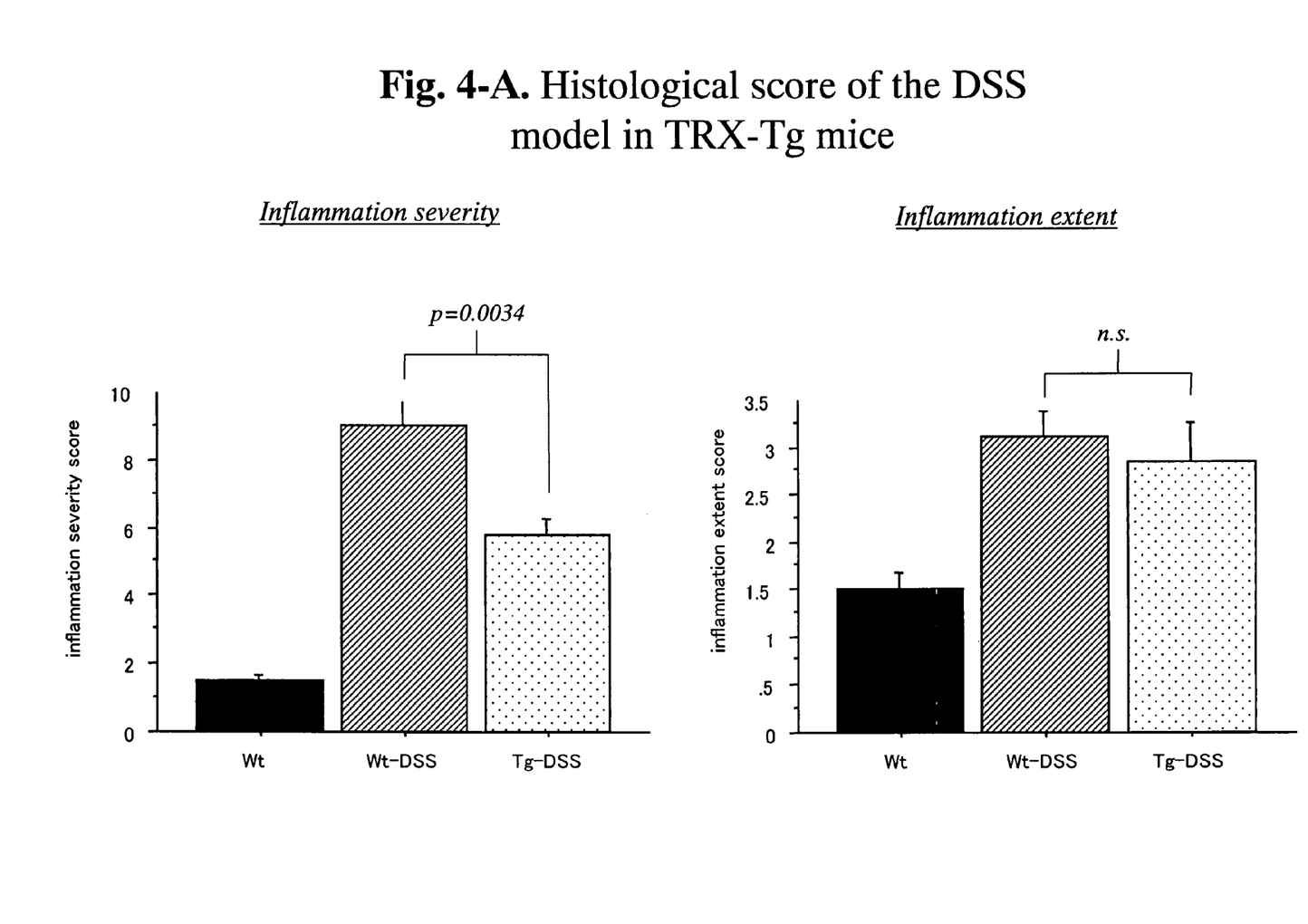

A histological investigation by HE staining revealed that inflammatory cell infiltration, crypt damage, and sore and ulcer formation were observed mainly in the distal colon in the Wt-DSS Group whereas the rectification of these symptoms was observed in the Tg-DSS Group (FIG. 3). Data points generated by the histological scoring system show significant rectification in the Tg Group with respect to "Inflammation Extent", "Crypt Damage" and "Total Colitis" (FIG. 4-A and B).

Example 2

Investigation of Therapeutic Effect of Recombinant Human Thioredoxin on DSS-Induced Colitis Model Mice C57BL/6 mice were given 3% (w/v) DSS in their drinking water for 5 days, and reared 5 more days with pure water till Day 10. These mice were weighed daily. From immediately before the beginning of DSS administration (Day 0), 150 µl of phosphate buffered saline (PBS) was intraperitoneally administered to the Control Group (n=10) every day, and 5 mg/kg of human recombinant thioredoxin dissolved in 150 µl PBS was intraperitoneally administered to the Treatment Group mice (n=10) every day. At Day 10 of the therapy, the mice were sacrificed by ether anesthesia, and the whole colons were removed to examine colitis.

Figure 5:
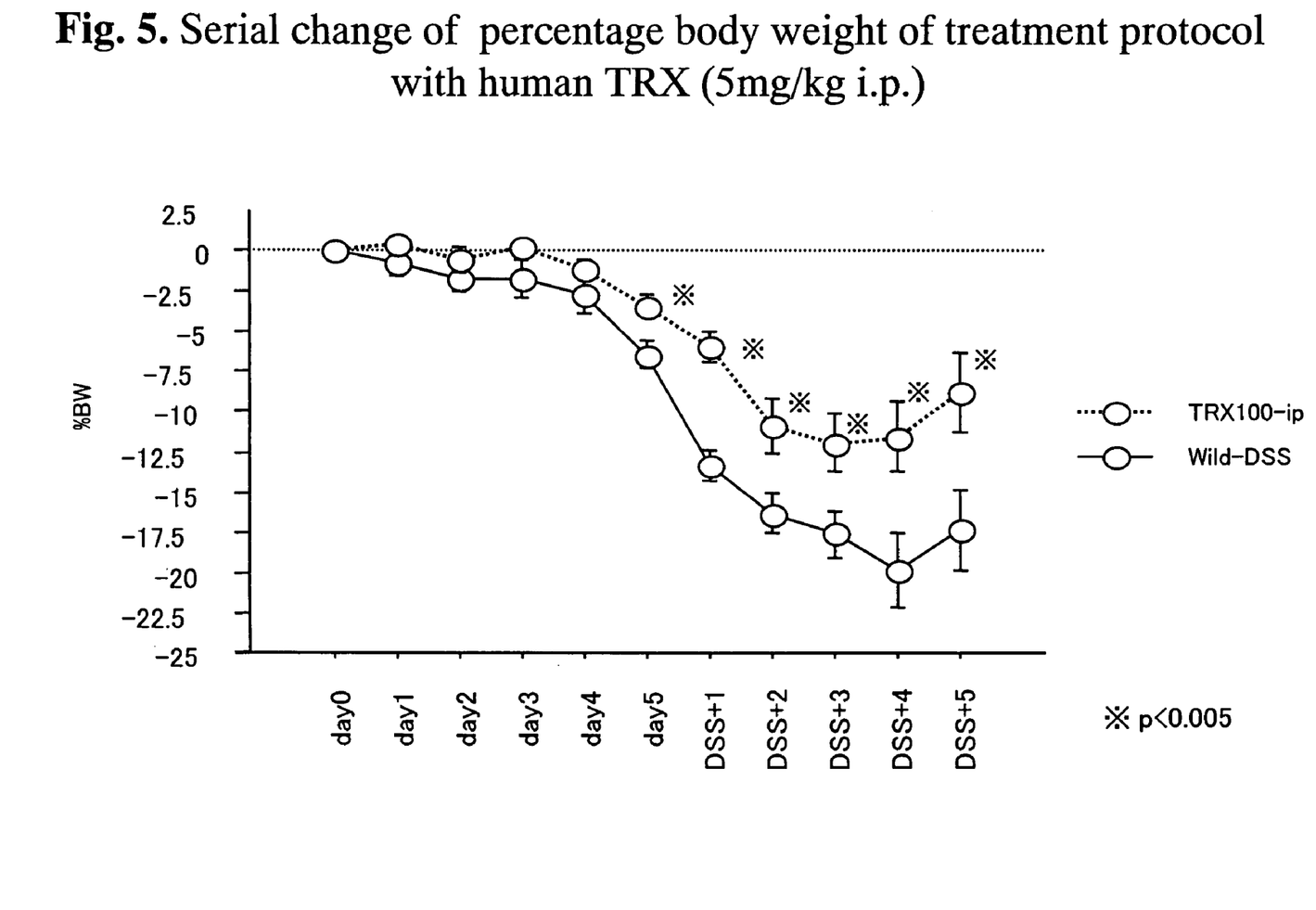
FIG. 5 shows the body weight changes of DSS colitis model mice and wild-type DSS colitis model mice (Wild-DSS) administered with rhTRX (TRX100-ip).
Figure 6:
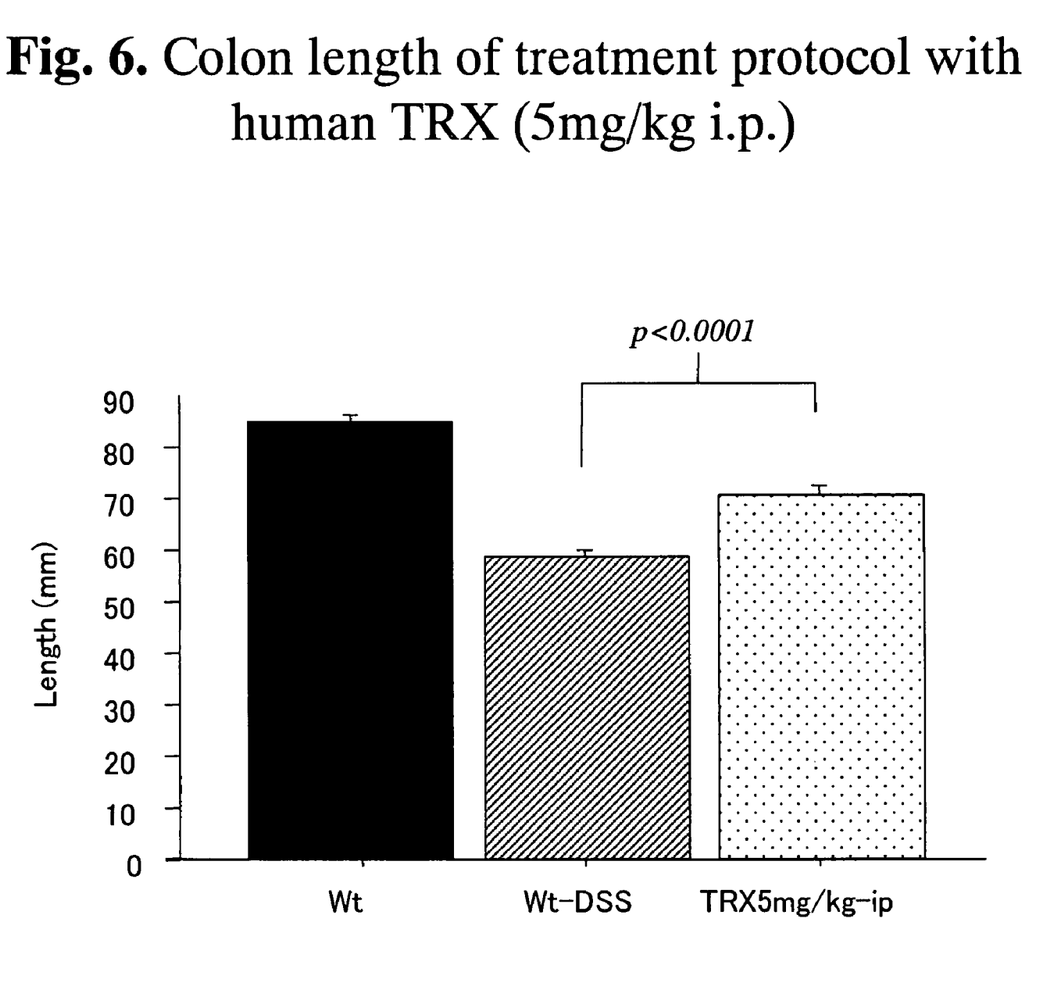
FIG. 6 shows the colon lengths of DSS colitis model mice administered with rhTRX (TRX 5 mg/kg-ip), wild-type DSS colitis model mice (Wt-DSS), and the control mice (Wt).

The weight reduction over Day 5 to Day 10 (DSS+5) after administration of DSS was significantly smaller in the Treatment Group than in the Control Group (FIG. 5). When measured, the average whole colon length of the Treatment Group was notably longer than that of the Control Group (FIG. 6).

Figure 7:
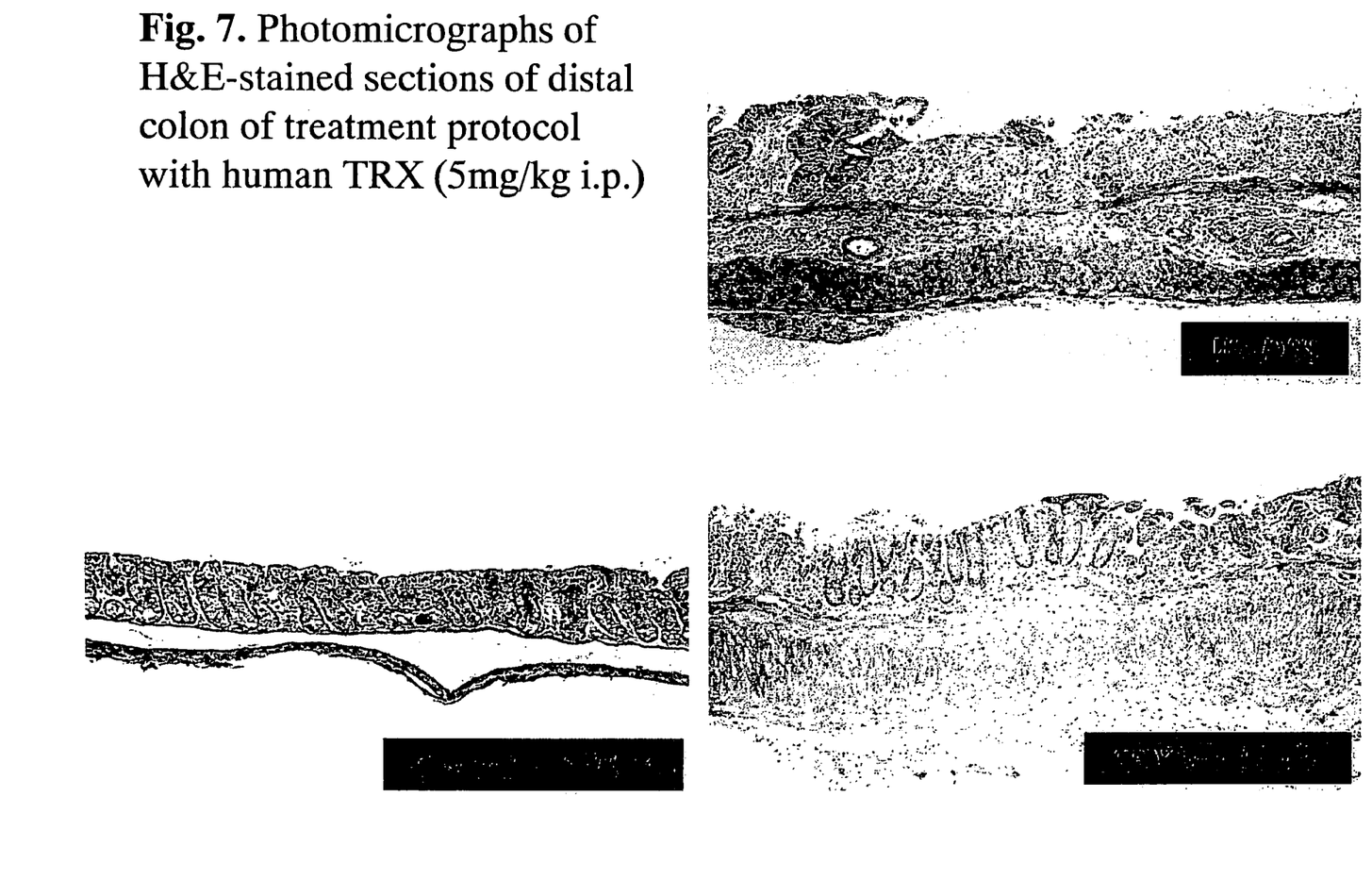
FIG. 7 shows HE (hematoxylin-eosin) staining of the distal colons of DSS colitis model mice administered with rhTRX (TRX 5 mg/kg i.p.), wild-type DSS colitis model mice (Wt-DSS), and the control mice (C57BL/6).
Figure 8:
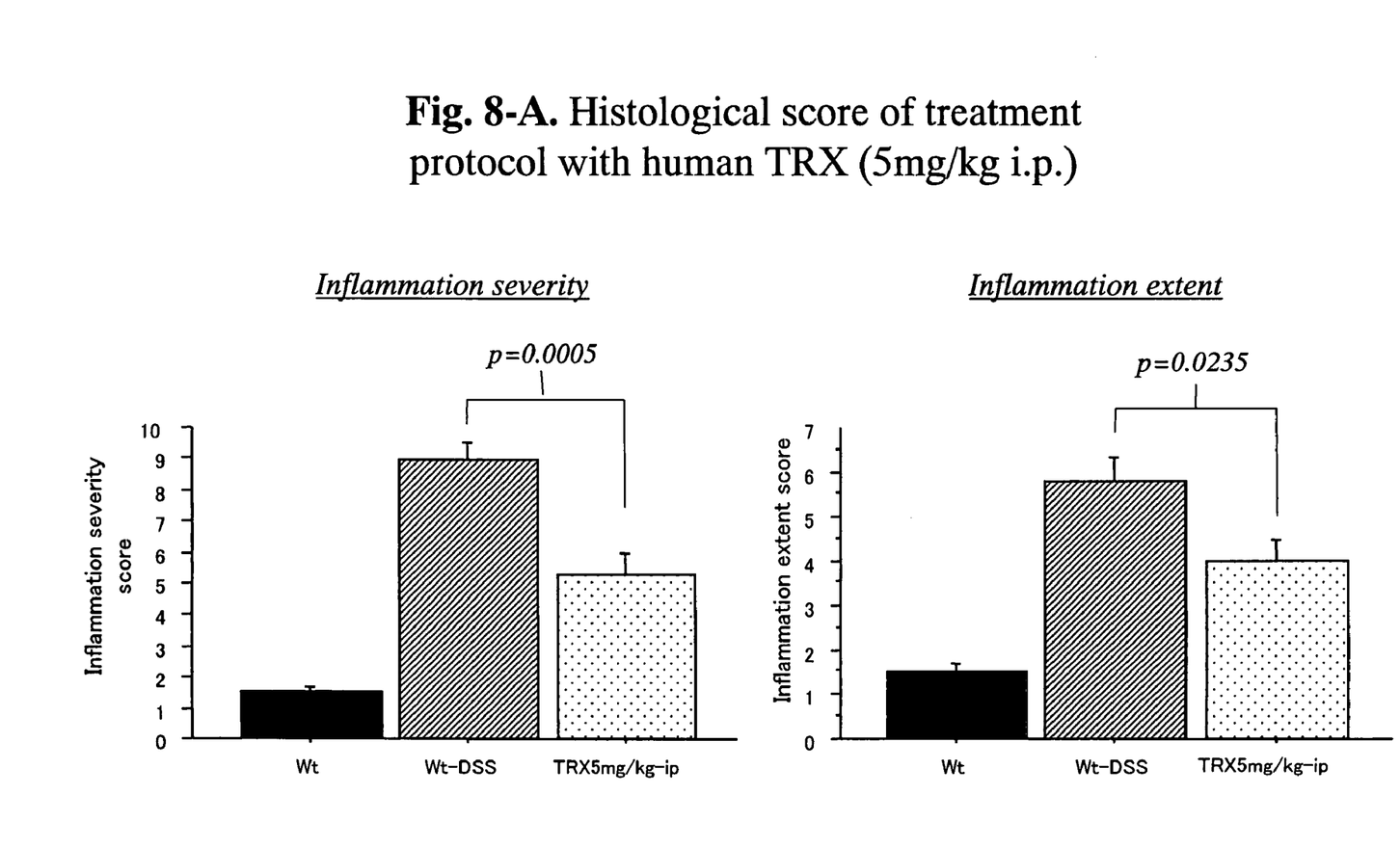

A histological investigation by HE staining revealed that the tissue damage observed in the Control Group was significantly rectified in the Treatment Group (FIG. 7). Data points generated by the Histological scoring system show significant rectification in the Treatment Group with respect to all categories Inflammation Severity, Inflammation Extent, Crypt Damage and Total Colitis (FIG. 8-A and B).

As demonstrated by the Examples, (1) the investigation using TRX-Tg mice showed the importance of TRX in colitis inhibition, and (2) therapeutical administration of TRX alone can rectify pathological conditions of colitis. These facts suggest the effectiveness of TRX as a therapeutic agent for treating inflammatory bowel diseases such as ulcerative colitis and the like.

INDUSTRIAL APPLICABILITY

The present invention provides a prophylactic and therapeutic agent for inflammatory bowel diseases that is free of side effects, using thioredoxin as an active ingredient, which is an endogenous thiol protein also produced within the living body. The present invention also provides a method for treating inflammatory bowel diseases using such an agent.

TABLE 1

Scoring system for bloody stool

| Score | Description |
|---|---|
| 0 | Normal to semisolid stool, no blood |
| 1 | Normal to semisolid stool, blood-tinged |
| 2 | Semisolid to fluid stool with definite evidence of blood |
| 3 | Bloody fluid |

TABLE 2

Histological scoring system for colitis

| Feature scored | Score | Description |
|---|---|---|
| Inflammation severity | 0 | None |
| | 1 | Mild |
| | 2 | Moderate |
| | 3 | Severe |
| Inflammation extent | 0 | None |
| | 1 | Mucosa |
| | 2 | Mucosa and submucosa |
| | 3 | Transmural |
| Crypt damage | 0 | None |
| | 1 | Basal ⅓ damaged |
| | 2 | Basal ⅔ damaged |
| | 3 | Crypts lost: surface epithelium present |
| | 4 | Crypts and surface epithelium lost |
| Percent involcement | 0 | 0% |
| | 1 | 1%-25% |
| | 2 | 26%-50% |
| | 3 | 51%-75% |
| | 4 | 75%-100% |

The invention claimed is:

1. A method for treating an inflammatory bowel disease, said method comprising administering an effective amount of polypeptide belonging to a thioredoxin superfamily to a patient in need thereof,
   said polypeptide comprising a sequence selected from the group consisting of SEQ ID NO:1, SEQ ID NO:3, SEQ ID NO:4, and SEQ ID NO:5.

2. The method according to claim 1, wherein the effective amount is 1-100 mg of polypeptide per kg body weight of a human adult.

3. The method according to claim 1, wherein said polypeptide is an isolated polypeptide comprising the sequence set forth in SEQ ID NO:1.

4. The method according to claim 1, wherein said polypeptide is in reduced form.

5. The method according to claim 1, wherein a solution or a suspension comprising said polypeptide is administered.

6. The method according to claim 1, wherein the polypeptide is human thioredoxin.

* * * * *

SEQUENCE LISTING

```
<160> NUMBER OF SEQ ID NOS: 5

<210> SEQ ID NO 1
<211> LENGTH: 4
<212> TYPE: PRT
<213> ORGANISM: Homo sapiens

<400> SEQUENCE: 1

Cys Gly Pro Cys
 1

<210> SEQ ID NO 2
<211> LENGTH: 4
<212> TYPE: PRT
<213> ORGANISM: Artificial Sequence
<220> FEATURE:
<223> OTHER INFORMATION: Consensus sequence in active site of TRX family
<220> FEATURE:
<221> NAME/KEY: VARIANT
<222> LOCATION: 2,3
<223> OTHER INFORMATION: Xaa = Any Amino Acid

<400> SEQUENCE: 2

Cys Xaa Xaa Cys
 1

<210> SEQ ID NO 3
<211> LENGTH: 4
<212> TYPE: PRT
<213> ORGANISM: Homo sapien

<400> SEQUENCE: 3
```

```
Cys Pro Thr Cys
 1

<210> SEQ ID NO 4
<211> LENGTH: 4
<212> TYPE: PRT
<213> ORGANISM: Homo sapien

<400> SEQUENCE: 4

Cys Pro His Cys
 1

<210> SEQ ID NO 5
<211> LENGTH: 4
<212> TYPE: PRT
<213> ORGANISM: Homo sapien

<400> SEQUENCE: 5

Cys Pro Pro Cys
 1
```